United States Patent [19]

Laborit

[11] 4,035,486

[45] July 12, 1977

[54] MEDICAMENT

[75] Inventor: Henri Laborit, Paris, France

[73] Assignee: Centre d'Etudes Experimentales et Clinques de Physio Biologie, de Pharmacologie et d'Eutonologie, C.E.P.B.E.P.E., France

[21] Appl. No.: 639,790

[22] Filed: Dec. 11, 1975

[30] Foreign Application Priority Data

Dec. 18, 1974  United Kingdom ............. 54582/74

[51] Int. Cl.² ........................................ A61K 37/26

[52] U.S. Cl. ............................... 424/178; 424/180; 424/311

[58] Field of Search ................... 424/178, 180, 311

[56] References Cited

PUBLICATIONS

Current Therapy – (1960) p. 305, W. B. Saunders Co., Phila. & London.

Primary Examiner—Frederick E. Waddell

[57] ABSTRACT

New medicament for regulating glycemia comprising guanosine associated with one of the compound of the group comprising acetylcholine and insulin.

2 Claims, 2 Drawing Figures

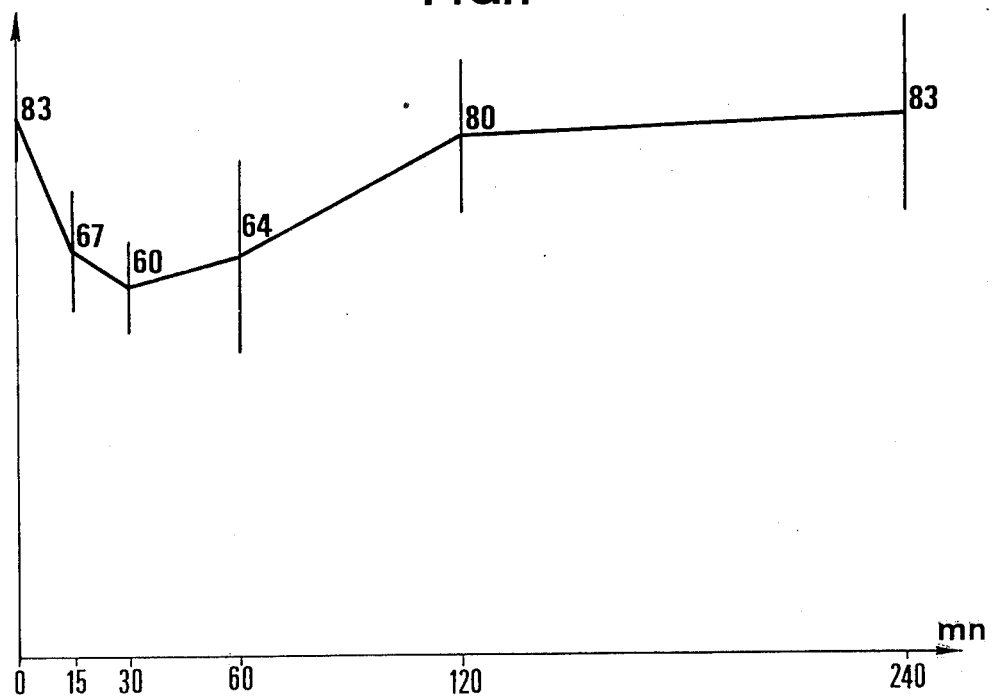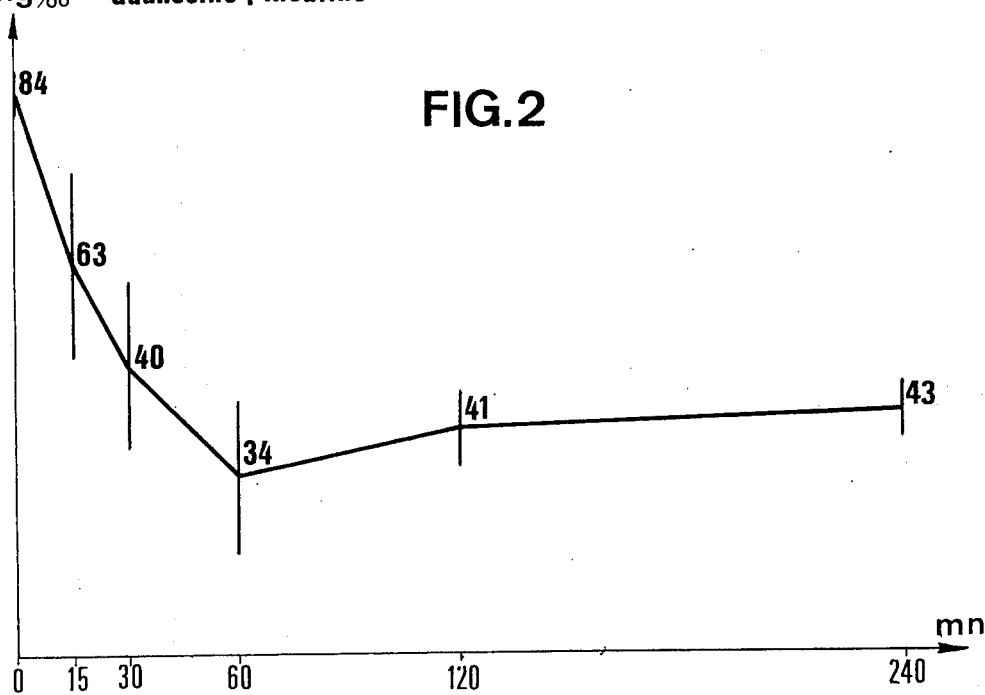

MEDICAMENT

The present invention relates to a new medicament for regulating glycemia.

The importance accorded nowadays, since the work of SUTHERLAND et al. ("Adrenergic Mechanisms" J. and A. Churchill Ltd. London — 1960 — pages 295 to 304). The importance to the variations in the intracellular concentration of 3′,5′-adenosine monophosphate (cyclic adenosine monophosphate or cAMP) is well-known. This compound, which originates in cells under the action of numerous hormones, biological or pharmacological molecules, seems to be the "second messenger" for the metabolic action of said molecules. It intervenes in the system for phosphorylating glycogen by enabling glucose-1-phosphate to be formed, and in the activity of organic tissue lipase.

More recently a study has been made of a related molecule, 3′,5′-guanosine monophosphate (cyclic guanosine monophosphate, or cGMP), in which properties that are generally antagonistic towards those of cAMP have been found. Certain facts even suggest that a high intracellular concentration of one prevents the formation, metabolism or action of the other (see in this connection the editorial in Nature, 1973, 246 : 186–187). However, the formation of cGMP from the action of a guanosine cyclase is caused by cholinergic agents (GEORGE, POLSON et al. Proc. Nat. Acad. Sci. — Washington — 1970, 66, 2: 398–403) and the insulin in the brain, heart, muscle and intestinal muscle of mammals (LEE, KUO et al. Proc. Nat. Acad. Sci. — Washington — 1972, 69, 11:3287–3291 and ILLIANO, TELL et al. (Proc. Nat. Acad. Sci. U.S.A. 70, 8: 2443–2447) whereas the formation of cAMP arises from the action of catecholaminergic agents, ACTH and glucagon.

The addition of adenoisine increases the accumulation of cAMP in the section of cerebral tissue (SATTIN and RALL, Molec. Pharmacol. 1970, 6 1: 13.23 and FERRENDELLI, KINSCHERF and CHANG, Molec. Pharmacol. 1973, 9, 4:445–454). It was thought that the administration of guanosine to animals in vivo, supplying a material which is abundant in the synthesis of cGMP, might perhaps increase the intracelluar formation of cGMP under the action of cholinergic stimulation or of insulin. The role of central neuromodulators, catecholaminergic and cholinergic ones in particular, dominates the behavioural activity. OLDS and MILNER (1954) and MARGULES and STEIN (Amer. J. Physiol. 1969, 217, 2:475–480) showed the significance in the central nervous action of two bundles: the medial forebrain bundle (MFB) and the periventricular system (PVS). The MFB would be the bundle of gratification, the bundle of reinforcement; it is catecholaminergic. The PVS would be the bundle of reaction to nociceptive stimulations, the bundle of punishment; it is cholinergic. It may be thought that, if the formation of the second chemical messenger, cGMP, is increased, there will be an increase in the excitability of the PVS and in the intensity of the organic reaction to agression. The pharmacological properties of guanosine have therefore been studied.

Research has shown that the association of guanosine with acetylcholine (ACh) or insulin causes increased metabolic activity in the ACh and insulin respectively.

According to the present invention therefore a medicament is provided comprising guanosine and either acetylcholine or insulin.

The invention is based on three experimental studies.

1. The investigation, on sections of a rat's brain which have been stimulated by KCl, of the variations in the consumption of oxygen, the production of lactic acid and the consumption of glucose, by WARBURG's conventional technique, after which these sections are subjected to the action of guanosine, ACh or insulin or guanosine in association with ACh or insulin.

2. The investigation of the content of glycogen in the brain of a mouse under the action of quanosine or insulin or these two agents in association.

3. The study of the variations in glycemia in a rabbit after an injection of either insulin or insulin in association with guanosine.

I. Action in vitro of guanosine, alone or in association with acetylcholine or insulin, on the consumption of oxygen, the accumulation of lactic acid and the consumption of glucose in sections of the cerebral cortex of a rat which have been stimulated by KCl.

Methods:

The animals which are used are male Wistar Vag rats with an average weight of 225/250 grammes, and they have been subjected to standard laboratory regime.

The sections of tissue, which weigh between 15 and 20 mg, were taken from the cerebral cortex of the rat and allowed to incubate for 1 hour at 37° after being placed in a flask containing the Krebs-Ringer phosphate buffer having a KCl concentration of 10 percent. The substrate comprises 15 $\mu$ moles of glucose. The guanosine, at a concentration of $1.166.10^{-4}$M, is added to the flask simultaneously with the glucose and the buffer, whereas the acetylcholine $2.7.10^{-10}$M and the insulin (Endopancrine) $66.10^{-4}$ $\mu$/liter are placed in the lateral paunch and put into contact with the section of tissue at a time 0. The total volume of the mixture is 3 mls.

The consumption of oxygen is measured according to Warburg's conventional method after a 1-hour period of incubation at 37°. It is expressed in $\mu$ moles of oxygen per hour and per gramme of tissue.

The lactic acid and glucose are determined in the deproteinised incubation medium by an enzymatic method. The results are expressed in $\mu$ moles/h/g of tissue.

Results:

The guanosine alone, with a concentration of $1.66.10^{-4}$M, has no effect upon the consumption of oxygen, the accumulation of lactic acid or the consumption of glucose in the sections of a rat's cerebral cortex; the results are not significantly different from those of the control experiments.

The acetylcholine alone with a concentration of $2.7.10^{-10}$M, increases the consumption of oxygen, this increase being accentuated by the association of guanosine with acetylcholine since it goes from 25 percent to 35 percent. The increase in the consumption of glucose caused by the acetylcholine alone is not modified by the addition of guanosine.

The association of guanosine with insulin $66.10^{-4}$ $\mu$/liter does not cause the consumption of oxygen to be increased significantly. On the other hand, the already considerable increase in the consumption of glucose under the action of insulin (50 percent) rises to 82 percent when insulin is associated with guanosine.

The results are set out in the following Table:

|  | Consumption of oxygen in moles/h/g of fresh tissue | Accumulation of lactic acid in moles/h/g of fresh tissue | Consumption of glucose in moles/h/g of fresh tissue |
|---|---|---|---|
| Control | $102.8 \pm 6.6$ | $85.2 \pm 4.5$ | $88.4 \pm 8.6$ |
| Guanosine $1.66.10^{-4}$M | $93.0 \pm 6.0$ | $88.2 \pm 5.4$ | $99.3 \pm 9.1$ |
| ACh $2.7.10^{-10}$M | $134.2 \pm 7.2$ | $98.8 \pm 3.7$ | $145.7 \pm 13.9$ |
| ACh $2.7.10^{-10}$M + Guanosine $1.66.10^{-4}$M | $162.1 \pm 13.9$ | $102.2 \pm 5.8$ | $138.0 \pm 10.6$ |
| Insulin $66.10^{-4}$ U/l | $91.6 \pm 5.3$ | $84.6 \pm 5.0$ | $168.5 \pm 17.0$ |
| Insulin $66.10^{-4}$U/l + Guanosine $1.66.10^{-4}$M | $125.6 \pm 7.5$ | $91.8 \pm 4.5$ | $194.9 \pm 17.5$ |

Action in vitro of guanosine alone, or in association with acetylcholine or insulin on the consumption of oxygen, accumulation of lactic acid and the consumption of glucose of the brain of a rat stimulated with KCl.

II – Values for the cerebral glycogen in a mouse after an injection of insulin associated with guanosine.

Material and methods:

The animals which are used are male mice with an average weight of 20–25 g.

Five groups of animals were studied which had received respectively:

1st group: a isotonic salt solution by intraperitoneal injection.

2nd group: a dose of 100 mg/kg of guanosine by intraperitoneal injection.

3rd group: a dose of 200 mg/kg of guanosine by intraperitoneal injection.

4th group: a dose of 0.5 $\mu$I/20 g per mouse of insulin by subcutaneous injection.

For these four groups the injection was made 30 minutes before the animals were killed.

5th group: an intraperitoneal injection of guanosine at a dose of 200 mg/kg 30 minutes before a sub-cutaneous injection of insulin at a dose of 0.5 $\mu$I/20 g per mouse.

The animal is killed 30 minutes after the second injection by being totally immersed in liquid nitrogen. The brains are removed whilst they are still deep-frozen.

The isolated glycogen is hydrolyzed by the enzyme amylo-$\alpha$-1,4-$\alpha$-1,6 glucosidase which releases the glucose by hydrolysis of the $\alpha$-(1 → 6) and $\alpha$-( → 4) bonds.

The glucose is then converted, in a single stage, to 6-phosphogluconate by the enzymes : hexokinase and glucose-6-phosphate dehydrogenase.

The formation of the nicotinamide adenine dinucleotide phosphate is then measured florometrically (NAHORSKI and ROGERS, Analyt. Biochem. 1972, 49, 492–497).

Results:

In the case of the animals treated with guanosine, either at a dose of 100 mg/kg or at a dose of 200 mg/kg, the levels of glycogen do not show any significant differences from the levels of the control animals. On the other hand, in the case of the animals treated with insulin, the level of glycogen is very much higher than that of the controls. The increase is significantly greater when insulin and guanosine are associated.

The results are illustrated in the following Table.

| Control isotonic salt solution | Guanosine 100 mg/kg | Guanosine 200 mg/kg | Insulin 0.5 I.U./20 g mouse | Insulin 0.5 I. U./20g. mouse + Guanosine 200 mg/kg. |
|---|---|---|---|---|
| $144 \pm 5$ (10) | $151 \pm 7$ (9) | $159 \pm 8$ (10) | $182 \pm 10$ (10) | $213 \pm 13$ (10) |

The number of animals is given in parenthesis.

The values of glycogen are expressed in $\mu$ g of glucose equivalents per g of frozen tissue.

Action of guanosine, insulin, insulin associated with guanosine on the glycogen of the mouse brain.

Control : Insulin $0.01 > P > 0.001$

Control : Insulin Guanosine $P > 0.001$

Insulin : Insulin guanosine $0.1 > P > 0.05$

III – Action of guanosine upon glycemia.

Material and Method:

The animals which are used are male rabbits with a weight of 2.200 kg to 2.500 kg.

Four groups of animals were studied which had received by intravenous injection, respectively, in a volume of 10 ml:

1st group: an isotonic solution of sodium chloride.

2nd group: guanosine at the rate of 100 mg per kg of rabbit.

3rd group: insulin at the rate of 0.5 I.U. per kg of rabbit.

4th group: guanosine at the rate of 100 mg per kg of rabbit and insulin at the rate of 0.5 I.U. per kg of rabbit.

A catheter is inserted into the femoral artery, its distal end being joined to the skin in the caudal region, such that the blood may be removed without harming the rabbit.

The drugs were injected via a vein in the ear. The guanosine was dissolved in an isotonic sodium chloride solution to which 1.5% NaOH was added until the guanosine has been dissolved. The pH of the final solution was 9.

After the inspection the rabbits were given 30 minutes rest.

Arterial blood was removed on six occasions at the times $t = 0$ min; $t = 15$ min; $t = 30$ min; $t = 60$ min; $t = 120$ min; $t = 240$ min.

The glycemia values were determined by the enzymatic method of BOEHRINGER.

Results:

The accompanying FIGS. I and II show that the association of guanosine and insulin increases significantly the drop in glycemia, compared with the drop in glycemia obtained with the same dose of insulin alone. Moreover, whilst in this latter case (FIG. I) the glycemia quickly returns to its original level it is found that when the insulin is associated with guanosine, the level of the glycemia is not raised again even at the 240th minute. If the probable increase in the formation of the cGMP under the action of the insulin and glucose in association is accepted, this increase appears to interfere with the processes for the homeostatic regulation of the glycemia.

All these results show that the metabolic activity of the ACh and insulin is increased by their association with guanosine. This is verified on the brain of the rat in virtro for the consumption of oxygen and glucose, and in vivo for insulin in the case of a mouse with regard to glycogenesis. In the rabbit, the action of insulin upon the glycemia is likewise intensified and prolonged. If one accepts that the cyclic guanosine monophosphate is the second messenger for the activity of these two hormones, one may think that the cellular provision, with guanosine, of a prematerial for its synthesis, may increase the organic tissue action of the ACh and the insulin.

If these results are interpreted in this manner, the use of guanosine in combination with cholinomimetics or insulin can be envisaged not only in the potentiation of the hypoglycemiant activity, but also in other fields. This is how STROM, BEAR and CARPENTER showed that physiological concentrations of insulin increased the ability of the cytotoxic lymphocytes to destroy the target cells, like cGMP and cholinomimetics. It is therefore possible to envisage the combination of guanosine with insulin to induce a potentiation of the immunitary defences. Conversely, WOLBERT, ZIMMERMAN et al. ascertained that the destruction in vitro of tumorous cells by mouse lymphocytes which have been specifically sensitized is inhibited by the adenosine which increases the intracellular concentration of cAMP. The anti-tumorous action of the guanosine/insulin combination thus merits attention. In cardiology, in cardiovascular reanimation, finally, it has been proposed to use the repolarizing combination of insulin + glucose + potassium salt (LABORIT, 1958). The addition of guanosine should increase the efficiency thereof.

What I claim is:

1. In an injectable medicament for regulating glucose metabolism in an animal with a compound selected from the group comprising acetylcholine and insulin, the improvement comprising the addition of a quantity of guanosine sufficient to increase the activity of said compound on the utilization of glucose by said animal.

2. In the method of regulating glucose glucose metabolism in an animal through the injection of insulin, the improvement comprising the associated injection of guanosine in an amount sufficient to increase the activity of insulin on the utilization of glucose by said animal.

* * * * *